(12) United States Patent
Powers et al.

(10) Patent No.: US 11,107,556 B2
(45) Date of Patent: Aug. 31, 2021

(54) AUTHORIZATION SYSTEM THAT PERMITS GRANULAR IDENTIFICATION OF, ACCESS TO, AND RECRUITMENT OF INDIVIDUALIZED GENOMIC DATA

(71) Applicant: HumanCode Inc., Denver, CO (US)

(72) Inventors: Rani K. Powers, Broomfield, CO (US); Christopher M. Glode, Denver, CO (US); Ryan P. Trunck, Denver, CO (US); Jennifer L. Lescallett, Sunderland, MD (US)

(73) Assignee: Helix OpCo, LLC, San Mateo, CA (US)

( * ) Notice: Subject to any disclaimer, the term of this patent is extended or adjusted under 35 U.S.C. 154(b) by 524 days.

(21) Appl. No.: 15/689,596

(22) Filed: Aug. 29, 2017

(65) Prior Publication Data
US 2019/0065679 A1   Feb. 28, 2019

(51) Int. Cl.
*G16B 50/00*   (2019.01)
*G16H 10/60*   (2018.01)
(Continued)

(52) U.S. Cl.
CPC .......... *G16B 50/00* (2019.02); *G06F 21/335* (2013.01); *G06F 21/602* (2013.01);
(Continued)

(58) Field of Classification Search
CPC ..... G16H 10/60; G06F 21/335; G06F 21/602; G06F 21/6263; H04L 29/06782;
(Continued)

(56) References Cited

U.S. PATENT DOCUMENTS 5,558,638 A * 9/1996 Evers ............... G16H 40/67
604/66
9,298,521 B1 * 3/2016 Feldman ........... G06F 3/0653
(Continued)

FOREIGN PATENT DOCUMENTS

WO   WO-2015027085 A1 * 2/2015   ............ G16B 40/00
WO   WO-2016149835 A1 * 9/2016   ......... G06F 21/6245

OTHER PUBLICATIONS

Elisha D.O. Roberson, Jonathan Pevsner, (2009) "Visualization of Shared Genomic Regions and Meiotic Recombination in High-Density SNP Data," PLoS ONE 4(8): e6711. doi:10.1371/journal.pone.0006711.
(Continued)

*Primary Examiner* — Jonathan Durant
*Assistant Examiner* — Anne-Marie K Alderson
(74) *Attorney, Agent, or Firm* — Duft & Bornsen, PC

(57) ABSTRACT

Systems and methods are provided for controlling dissemination of genomic data. One embodiment is a system that stores genomic data. The genomic data for each individual lists genetic variants determined to exist within that individual. The system receives an access request for a segment of genomic data for an individual, analyzes an authentication token within the request, authenticates the request as belonging to an account for a user based on the authentication token, and reviews authorization directives for the individual that indicate how predefined portions of genomic data are shared. The system also transmits the segment of genomic data in response to determining that the authorization directives permit the account to access the segment of genomic data, and prevents transmission of the segment of genomic data in response to determining that the authorization directives do not permit the account to access the segment of genomic data.

20 Claims, 12 Drawing Sheets

(51) Int. Cl.
*H04L 29/06* (2006.01)
*G06F 21/62* (2013.01)
*G06F 21/60* (2013.01)
*G06F 21/33* (2013.01)
*G16B 50/30* (2019.01)

(52) U.S. Cl.
CPC ......... *G06F 21/6263* (2013.01); *G16B 50/30* (2019.02); *G16H 10/60* (2018.01); *H04L 29/06782* (2013.01); *H04L 29/06809* (2013.01); *H04L 29/06836* (2013.01); *H04L 63/083* (2013.01); *H04L 63/102* (2013.01)

(58) Field of Classification Search
CPC ......... H04L 29/06809; H04L 29/06836; H04L 63/083; H04L 63/102; G16B 50/00; G16B 50/30
See application file for complete search history.

(56) References Cited

U.S. PATENT DOCUMENTS

| | | | | |
|---|---|---|---|---|
| 2008/0172737 | A1* | 7/2008 | Shen | G06F 21/6245 726/21 |
| 2011/0257896 | A1* | 10/2011 | Dowds | G16B 45/00 702/20 |
| 2011/0295694 | A1* | 12/2011 | Coggeshall | G06Q 30/0273 705/14.66 |
| 2015/0227697 | A1* | 8/2015 | Nelson | G16H 40/63 705/3 |
| 2015/0244687 | A1* | 8/2015 | Perez | G16H 10/60 726/4 |
| 2015/0310174 | A1* | 10/2015 | Coudert | G16H 10/60 705/3 |
| 2016/0117448 | A1* | 4/2016 | Van De Craen | G16H 10/60 705/3 |
| 2017/0255790 | A1* | 9/2017 | Barrett | G16B 20/20 |
| 2017/0329891 | A1* | 11/2017 | Macpherson | G16B 10/00 |
| 2018/0046753 | A1* | 2/2018 | Shelton | G16H 50/70 |

OTHER PUBLICATIONS

Anonymous, "Haplotype," Wikipedia. Online at https://en.wikipedia.org/wiki/Haplotype, retrieved on Jul. 24, 2017.
Anonymous, "Haplogroup," Wikipedia. Online at https://en.wikipedia.org/wiki/Haplogroup, retrieved on Jul. 24, 2017.
Anonymous, "Autosomal DNA statistics" ISOGG Wiki, Online at https://isogg.org/wiki/Autosomal_DNA_statistics, retrieved on Jul. 24, 2017.
Hill, WG & Weir, BS 2011, "Variation in actual relationship as a consequence of Mendelian sampling and linkage", Genetics Research, vol. 93, No. 1, pp. 47-64. Doi: 10.1017/S0016672310000480.
Anonymous, "Autosomal DNA" ISOGG Wiki, Online at https://isogg.org/wiki/Autosomal_DNA, retrieved on Jul. 24, 2017.
Anonymous, "Authorization: conceptual model", IBM, Online at https://www.ibm.com/support/knowledgecenter/en/SSPREK_9.0.0/com.ibm.isam.doc/base_admin/concept/con_authocncptmdl.html, retrieved on Jul. 24, 2017.
Anonymous, "Share and Compare Basics" 23andMe, Online at https://customercare.23andme.com/hc/en-us/articles/212870697-Share-and-Compare-Basics, retrieved on Jul. 24, 2017.
Anonymous, "Sharing DNA Results," Ancestry.com, Online at https://support.ancestry.com/s/article/ka215000000MVhaAAG/Sharing-my-Full-AncestryDNA-results-1460088592896-2580, retrieved Jul. 6, 2017.
Anonymous, "IGSR: The International Genome Sample Resource," Online at http://www.internationalgenome.org/wiki/Analysis/vcf4.0/, retrieved Jul. 19, 2017.
Anonymous, "Frequently Asked Questions: Data File Formats" Ensembl, Online at http://www.ensembl.org/info/website/upload/bed.html, retrieved Jul. 19, 2017.
Anonymous, "Share and Compare," 23andMe, Online at you.23andme.com/tools/share/manage, retrieved on Aug. 9, 2017.

* cited by examiner

AUTHENTICATION DIRECTIVES

FIG. 10

VARIANT CALL FORMAT

```
##fileformat=VCFv4.0
##fileDate=201707019
##source=GENDATSRVR
##permitted_days=14
##individual=65134
##INFO=<ID=GN=1,Type=Integer,Description="GENE TAG">
##FILTER=<ID=PRICE,Description="PRICE PERMITTED FOR USE OF GENOMIC DATA IN STUDIES">
##FORMAT=<ID=PANEL,Number=.,Type=STRING,Description="GENETIC PANEL">
##FORMAT=<ID=R,Number=.,Type=FLOAT,Description="RANK">
```

| #CHROM | POS   | ID        | REF  | ALT    | QUAL | FILTER | INFO             | FORMAT   | NA00001            |
|--------|-------|-----------|------|--------|------|--------|------------------|----------|--------------------|
| 12     | 14970 | rs4043257 | C    | G      | 15   | PASS   | GN=1256;         | PANEL:R  | CANCER\|0.95       |
| 01     | 17730 | .         | G    | T      | 54   | PRICE  | GN=25; AA=G;     | PANEL    | ANCESTRY           |
| 16     | 11804 | rs9125214 | T    | C,G    | 92   | PASS   | GN=1207;         | PANEL    | PREGNANCY          |
| 21     | 22302 | .         | A    | .      | 14   | PASS   | GN=5307          | PANEL:R  | METABOLISM\|0.237  |
| 15     | 72345 | plan1     | GTCT | G,CGAC | 76   | PASS   | GN=702           | PANEL    | METABOLISM         |

1010, 1030, 1020, 1040, 1050

1000

FIG. 11
BROWSER EXTENSIBLE DATA

| | |
|---|---|
| | browser position chr15:165473324-165478964 |
| | browser hide all |
| | track name="DA_7-19-2027" description="delete the following sequences after July 19, 2027" |
| 1110 | chr15   1654733324   1654733324   SNP32   0   - |
| 1120 | chr15   1654733381   1654733395   SEQ15   0   + |
| | chr15   1654733399   1654733399   SNP95   0   - |
| | chr15   1654733561   1654733561   SNP21   0   + |
| | chr15   1654733562   1654733579   SEQ51   0   + |
| 1110 | track name="DA_NEVER" description="maintain the following sequences in perpetuity without deleting" |
| 1120 | chr15   1654774002   1654774004   SEQ07   0   - |
| | chr15   1654775931   1654776042   SEQ76   0   + |
| | chr15   1654776212   1654776212   SNP29   0   + |
| | chr15   1654777498   1654777999   SEQ25   0   - |

1100

AUTHORIZATION SYSTEM THAT PERMITS GRANULAR IDENTIFICATION OF, ACCESS TO, AND RECRUITMENT OF INDIVIDUALIZED GENOMIC DATA

FIELD

The disclosure relates to the field of genomics, and in particular, to techniques that enable individuals to define how their genomic data is shared.

BACKGROUND

The genes of individuals code for a variety of proteins. The expression of a gene in messenger ribonucleic acid (mRNA) and protein contributes to a variety of phenotypic traits (i.e., observable traits such as eye color, hair color, etc.). If a variation occurs in a specific gene, that variation is reflected in mRNA and protein, which can result in a different phenotype. Genetic factors therefore play a major role in a variety of phenotypic traits. For example, normal variations (polymorphisms) in two genes, EDAR and FGFR2, have been associated with differences in hair thickness.

Because genes act as blueprints for the fundamental operational components of the human body, individuals may engage in genetic testing to identify medical conditions, to determine ancestry, or even to sate their own curiosity about traits related to appearance, wellness, etc. The genome of an individual is particularly hard to interpret without the advice of expert systems or individuals. At the same time, the genome of an individual is very private. Hence, the sharing of personalized genomic data remains problematic because it forces individuals to balance their desire for knowledge against their desire for privacy. This may place a chilling effect on the exchange of genomic data, which inhibits the overall progress of the field of genetic research and development.

Thus, individuals continue to seek out systems and techniques that provide a balance between sharing genomic data and ensuring the preservation of individual privacy.

SUMMARY

Embodiments described herein provide for enhanced systems and techniques that enable selective authentication and authorization of requests that are directed to the genomic data of individuals. For example, these techniques may allow an individual to provide authorization to specific portions of their genome, on a user-by-user basis, device-by-device basis, and/or for predefined periods of time. Techniques discussed herein may even analyze a requesting user's genome in order to determine a familial relationship between the requesting user and the individual whose genomic data is being requested. The system may then provide authorization to access the genomic data based on the familial relationship.

One embodiment is a system that includes a genomic data server that stores genomic data for multiple individuals. The genomic data for each individual lists genetic variants determined to exist within that individual. The system also includes a genomic authorization server. The genomic authorization server includes an interface that receives an access request for a segment of genomic data for an individual, and a controller that analyzes an authentication token within the request, authenticates the request as belonging to an account for a user based on the authentication token, and reviews authorization directives for the individual that indicate how predefined portions of genomic data are shared. The controller transmits the segment of genomic data in response to determining that the authorization directives permit the account to access the segment of genomic data, and the controller prevents transmission of the segment of genomic data in response to determining that the authorization directives do not permit the account to access the segment of genomic data.

A further embodiment is a method. The method includes storing genomic data for multiple individuals. The genomic data for each individual lists genetic variants determined to exist within that individual. The method further includes receiving an access request for a segment of genomic data for an individual, analyzing an authentication token within the request, and authenticating the request as belonging to an account for a user based on the authentication token. Additionally, the method includes reviewing authorization directives for the individual that indicate how predefined portions of genomic data are shared, transmitting the segment of genomic data if the authorization directives permit the account to access the segment of genomic data, and preventing transmission of the segment of genomic data if the authorization directives do not permit the account to access the segment of genomic data.

A further embodiment is a non-transitory computer readable medium embodying programmed instructions which, when executed by a processor, are operable for performing a method. The method includes storing genomic data for multiple individuals. The genomic data for each individual lists genetic variants determined to exist within that individual. The method further includes receiving an access request for a segment of genomic data for an individual, analyzing an authentication token within the request, and authenticating the request as belonging to an account for a user based on the authentication token. Additionally, the method includes reviewing authorization directives for the individual that indicate how predefined portions of genomic data are shared, transmitting the segment of genomic data if the authorization directives permit the account to access the segment of genomic data, and preventing transmission of the segment of genomic data if the authorization directives do not permit the account to access the segment of genomic data.

Other exemplary embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

FIG. 10 is a block diagram illustrating a customized Variant Call Format (VCF) file that includes sharing parameters in an exemplary embodiment.

FIG. 11 is a block diagram illustrating a customized Browser Extensible Data (BED) file that includes sharing parameters in an exemplary embodiment.

DESCRIPTION

The figures and the following description illustrate specific exemplary embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1:
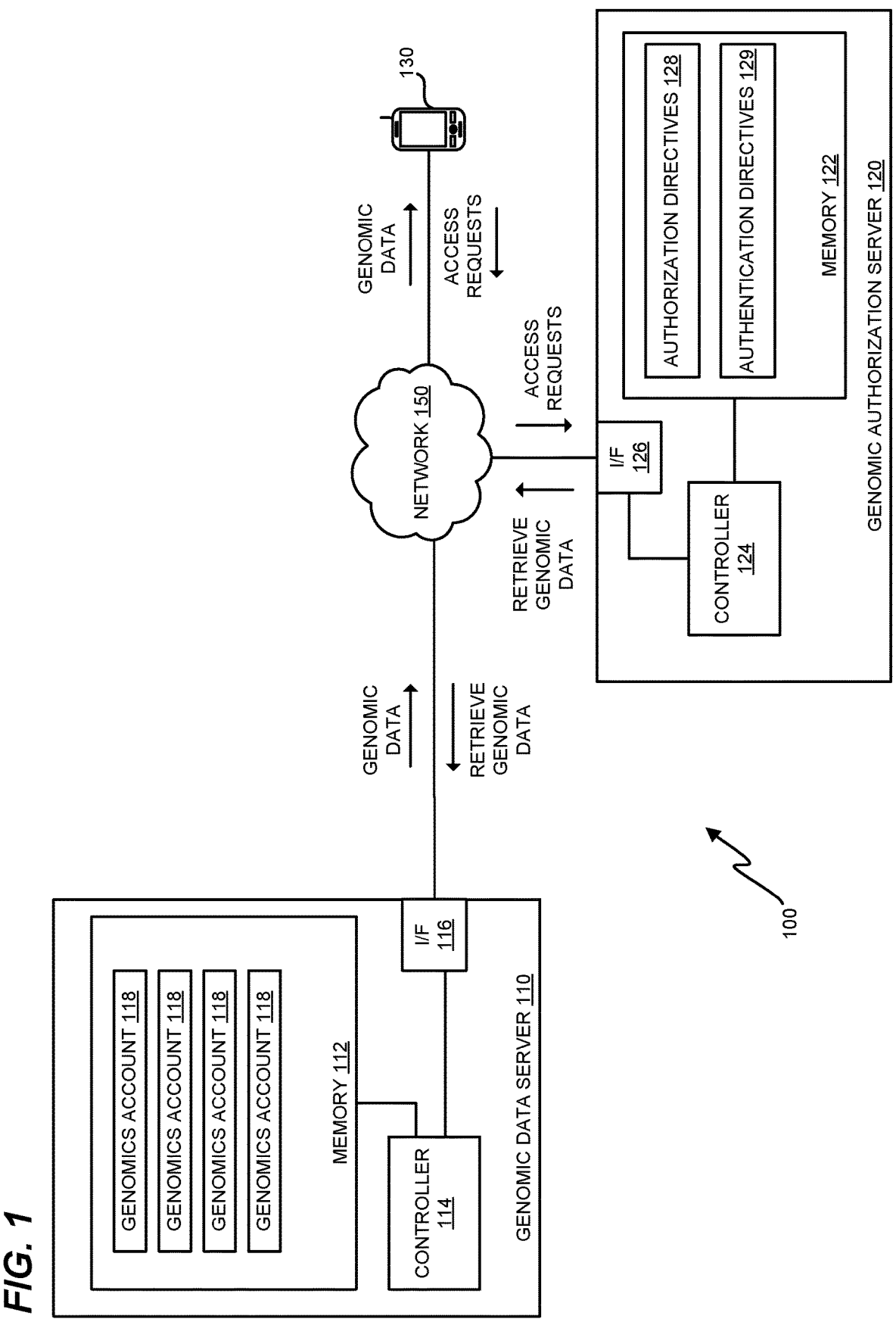
FIG. 1 is a block diagram of a genomic sharing system in an exemplary embodiment.

FIG. 1 is a block diagram of a genomic sharing system 100 in an exemplary embodiment. Genomic sharing system 100 comprises any combination of systems, components, or devices that selectively shares genomic data with one or more users. As used herein, the term "genomic data" refers to known genetic variants found within specific individuals. Furthermore, the term "genetic variant" refers to a variation of an individual gene (e.g., an allele) or any area that differs between the genomes of individuals. Such variants may include Single Nucleotide Polymorphisms (SNPs), structural variants such as insertions and deletions, Copy Number Variants (CNVs), etc., and hence may include variations in nucleotides that regulate gene expression or gene activity. Thus, a specific pattern of base pairs within a gene (e.g., "GCTTAGAC"), a specific base pair (e.g., "C") at a SNP, and other genetic variants found within an individual qualify as genomic data for that individual.

In this embodiment, genomic sharing system 100 includes genomic data server 110, genomic authorization server 120, and one or more devices 130 that access genomic data server 110 and genomic authorization server 120 via network 150 (e.g., the Internet, a private network, a Wireless Local Area Network (WLAN), etc.).

Device 130 (e.g., a general purpose computer, server, laptop, tablet, cellular phone, etc.) receives input from a user that has an account registered at genomic authorization server. Based on this input, device 130 generates an access request for acquiring genomic data from genomics accounts 118 stored in memory 112 of genomic data server 110. Each genomics account 118 lists the genetic variants found within a specific individual, and may include the entire genome of that individual. For example, a genomics account 118 in memory 112 may indicate known genetic variants found within a specific individual (e.g., entire sequences, or variants of unknown significance), and different genomics accounts 118 may correspond with different individuals. Thus, batches of genomics accounts 118 may report the existence (or non-existence) of specific genetic variants for a large number of specified individuals. Genomics accounts 118 may further report which specific allele(s) are within the genome of an individual (for example, to facilitate analysis of SNPs that are triallelic). For CNVs, genomics accounts 118 may also report the number of copies of the CNV found in the genome of the individual, rather than just presence or absence of the CNV.

The access request generated at device 130 is transmitted via network 150 to interface (I/F) 126 of genomic authorization server 120. Controller 124 authenticates the access request. The authentication process ensures that the access request has actually been generated by the account listed in the access request. That is, the authentication process ensures that the access request has not been "spoofed" so that it appears to have come from a different account. Controller 124 performs these operations based on authentication directives 129 stored in memory 122.

Authorization server 120 also determines whether or not the account has permission to access the genomic data identified in the request. This is performed based on authorization directives 128. If the user is authenticated and authorized to access the requested genomic data, controller 124 generates a command to retrieve genomic data from one or more genomics accounts 118. The command is transmitted from I/F 126 to network 150, and is received at I/F 116 of genomic data server 110. Controller 114 at genomic data server 110 generates a response that includes the requested genomic data indicated in the command, and directs I/F 116 to transmit the response to genomic authorization server 120. The response may then be packaged (e.g., by encrypting the response or appending an expiration date to the response), and transmitted to device 130 via genomic authorization server 120. Device 130 processes the response (e.g., based on a stored app at device 130, or other program operating at device 130), and provides genomic data and/or analysis to the user.

I/F 116 and I/F 126 comprise any suitable components for transmitting data, such as Ethernet ports, wireless transceivers compatible with IEEE 802.11 protocols, etc. Controller 114 and controller 124 may be implemented, for example, as custom circuitry, as a hardware processor executing programmed instructions, or some combination thereof. While only one device 130 is discussed above, in further embodiments any suitable number of devices 130 may utilize genomic sharing system 100.

Figure 2:
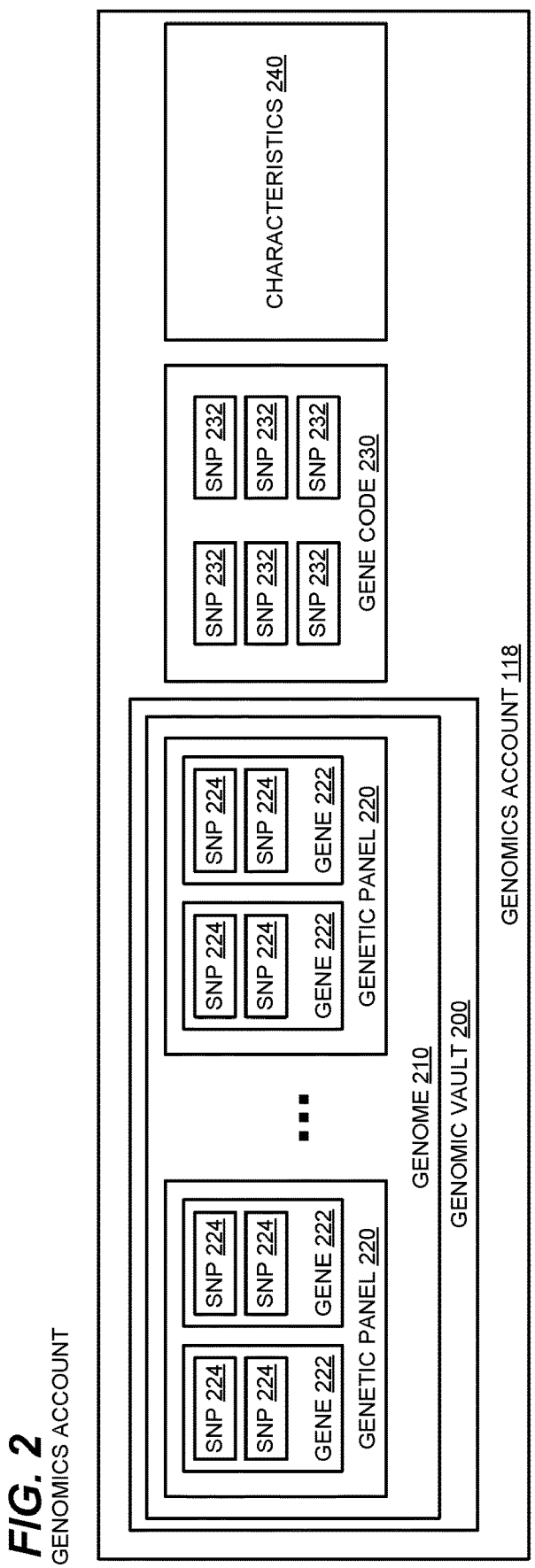
FIG. 2 is a block diagram illustrating contents of a genomics account in an exemplary embodiment.
Figure 3:
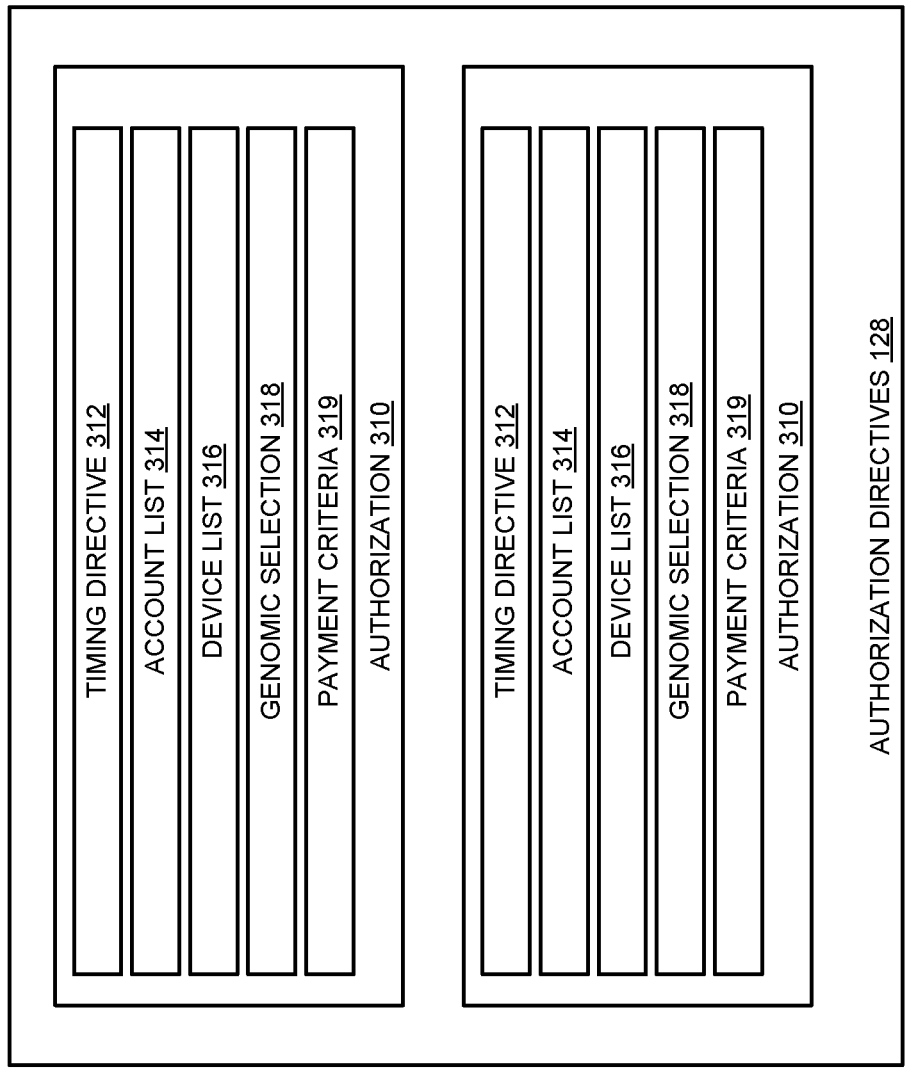
FIG. 3 is a block diagram illustrating authorization directives for genomic sharing in an exemplary embodiment.
Figure 4:
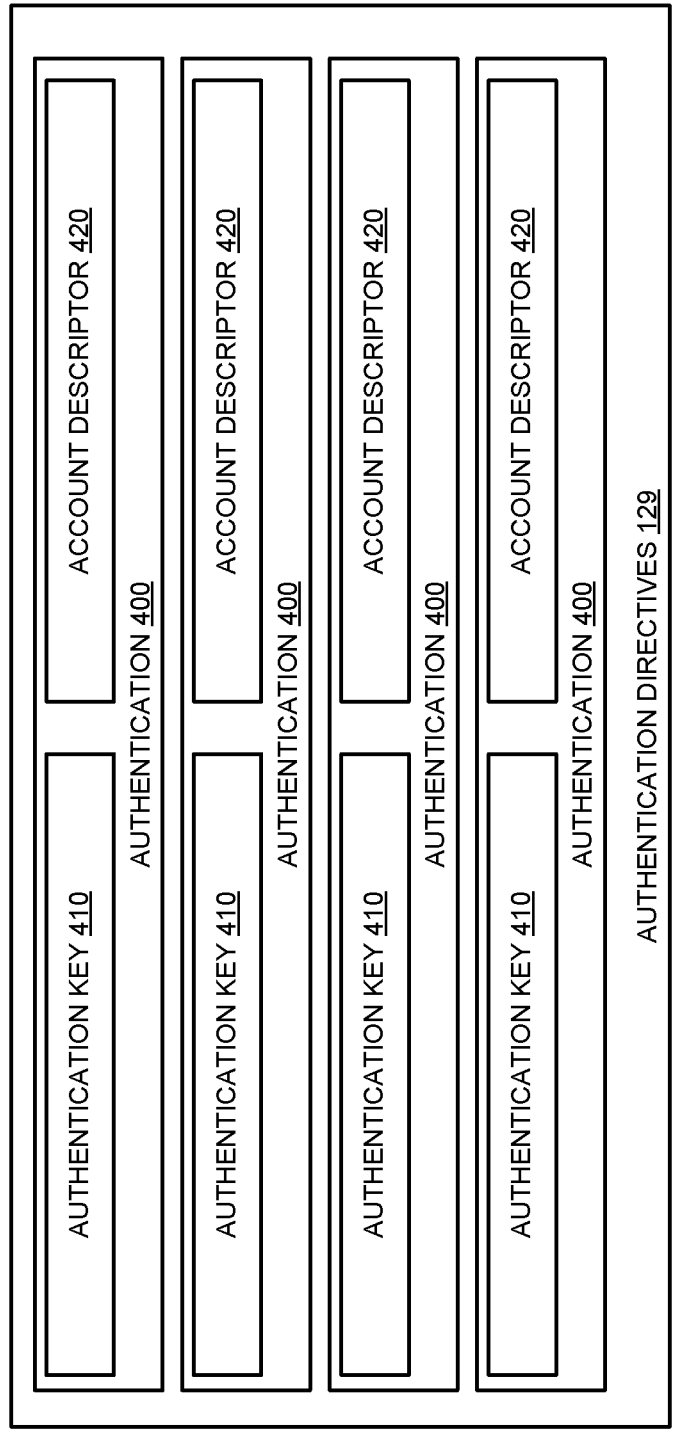
FIG. 4 is a block diagram illustrating authentication directives for genomic sharing in an exemplary embodiment.

FIGS. 2-4 illustrate further features of the genomics accounts, authentication directives, and authorization directives discussed above. Specifically, FIG. 2 is a block diagram illustrating contents of a genomics account 118 in an exemplary embodiment. In this embodiment, each genomics account 118 corresponds with a specific individual. Furthermore, each genomics account 118 is subdivided into genomic vault 200, gene code 230, and characteristics 240. Genomic vault 200 stores genome 210 (e.g., an entire genome of the individual, or a curated subset of the genome), and genomic vault 200 may comprise an encrypted container or file in which genomic data is stored. Genome 210 is subdivided into predefined genetic panels 220. Each genetic panel 220 may correspond, for example, with a different category of genetic information, such as maternity, fitness, metabolism, sleep, ancestry, phenotypes defined by genomic data (e.g., appearance), cancer, etc. Each genetic panel 220 includes genomic data (e.g., genetic variants of genes 222, SNPs 224, etc.) affiliated with the corresponding category. This subdivision of genome 210 into genetic panels 220 enables access to genomic data to be finely grained. For example, permissions/authorization may be defined on a whole genome basis, on a panel-by-panel basis, on a gene-by-gene basis, on a SNP-by-SNP basis, etc. as desired by an individual.

Gene code 230 is a selected portion of genome 210 that is compared with a gene code of a user in order to determine the existence of a familial relationship. Gene code 230 may include predefined SNPs and/or genes that are highly conserved. For example, gene code 230 may include SNPs that vary little between members of a family group (e.g., SNPs in gene code 230 may correspond with one or more haplotypes). In this embodiment, gene code 230 includes SNPs 232. The number and selection of SNPs 232 used for gene code 230 may vary depending upon the specificity with which familial relationships are desired to be determined. In further embodiments, gene code 230 comprises pointers to SNPs that are maintained in genome 210.

Genomics account 118 may also store characteristics 240 of the individual. As used herein, a "characteristic" of an individual include phenotypes exhibited by an individual, such as hair color, eye color, height, etc. Characteristics also include behaviors of the individual such as fitness patterns, dietary habits, travel patterns, social networking behaviors and preferences (e.g. "Likes" of a sports team or political party), etc. Characteristics may even include the name of an individual, or the "digital footprint" of an individual, such as interactions with others on a social network, financial transactions performed by the individual, a history of medical treatment for the individual, etc.

FIG. 3 is a block diagram illustrating authorization directives 128 for genomic sharing in an exemplary embodiment. Like genomics accounts 118, each set of authorization directives 128 may correspond with a different individual. However, while genomics accounts 118 each indicate the genetic variants of a specific individual, each set of authorization directives 128 indicates how an individual desires his or her genomic data (and/or other characteristics) to be shared. The set of authorization directives 128 for an individual is subdivided into authorizations 310. A user may access genomic data if their access request meets the requirements of at least one of authorizations 310.

In this embodiment, each authorization 310 includes parameters such as a timing directive 312, account list 314, device list 316, genomic selection 318, and/or payment criteria 319. Each authorization 310 need not include all of the parameters discussed above, but rather may include any suitable combination thereof. Furthermore, the various parameters of an authorization 310 may be logically combined (e.g., with logical AND operators, logical OR operators, etc.) as desired in order to create a Boolean statement that evaluates whether the authorization for an incoming request is granted or denied.

Timing directive 312 indicates one or more periods of time during which the authorization 310 is granted (e.g., a predefined period of days, months, years, etc.). In one embodiment, timing directive 312 describes a time period with a predefined start date and end date. In a further embodiment, the time period is defined as a length of time. The time period starts from the date and time that genomic data is shared with a specific account. The time period may therefore have different start and end times for different accounts, depending on when each account first utilized the authorization 310.

Account list 314 provides a list of accounts that are granted access by authorization 310. Accounts that are not indicated on account list 314 are not permitted to use the authorization 310 to access data from a corresponding genomics account 118. In one embodiment, each account is associated with one or more tags (e.g., fitness, research, physician, family member, lawyer), and account list 314 provides a list of tags for which authorization is granted. Device list 316 provides a list of specific devices (e.g., by Media Access Control (MAC) address) and/or device types (e.g., laptops, tablets, cellular phones, media players) for which the authorization 310 is granted. Devices that are not indicated in device list 316 may not use the authorization 310 to access data from the corresponding genomics account 118.

Genomic selection 318 indicates predefined portions of genomics account 118 that authorization 310 grants access to. Thus, different authorizations 310 may pertain to different genetic panels, genes, or SNPS to provide for a highly granular access scheme. Payment criteria 319 indicates a price at which sharing of genomic data from genomic selection 318 may be achieved. In one embodiment, payment criteria 319 may grant access in a manner that bypasses account list 314 and device list 316 parameters provided in authorization 310. In a further embodiment, payment criteria 319 includes a flag indicating whether the price may be bypassed when an access request is for non-profit research purposes. Other flags (e.g., for cancer research, fertility research, intelligence research, for-profit research) may also be utilized in order to bypass price for specific fields of research. In further embodiments, specialized flags may set such that each flag specifically volunteers genomic selection 318 for sharing with a specific study.

Other parameters (e.g., device location, lists of prohibited accounts, lists of allowed applications, keyphrases, a selection of characteristics to share, etc.) may also be utilized within an authorization 310. For example, additional parameters may be utilized to grant a limited number of accesses (e.g., one-time access), a limited number of accesses per time period (e.g., one access per month), etc.

By defining multiple authorizations 310 that each correspond with a different genomic selection, an individual may carefully tailor how others may interact with her or his genomic data. This may help to facilitate the sharing of certain genetic variants for specifically tailored purposes, according to specifically tailored times and circumstances, in order to ensure that that no portions of the individual's genome are overshared or exploited.

FIG. 4 is a block diagram illustrating authentication directives 129 for genomic sharing in an exemplary embodiment. While FIG. 2 illustrates a genomics account 118 storing genomic data for an individual, and FIG. 3 illustrates authorization directives 128 that indicate how subsets of genomic data may be shared with others, FIG. 4 illustrates how access requests may be authenticated.

In this embodiment, authentication directives 129 include multiple authentications 400. Each authentication 400 includes an authentication key 410, which may comprise an encrypted key (e.g., a key of a key pair, such as a public key, private key, etc.). In further embodiments, an authentication key 410 may comprise a password, a biometric parameter (e.g., fingerprint, retina map, DNA sequence), etc. Each authentication 400 also includes an account descriptor 420, which lists the account associated with the authentication key 410. In this manner, if an access request includes a key that corresponds with (e.g., is paired with, exactly matches, etc.) authentication key 410, controller 124 of genomic authorization server 120 may determine that the access request originated from the associated account.

With an explanation of the various components of genomic sharing system 100 described above, further discussion turns to the operation of genomic sharing system 100 in selectively permitting access to genomic data, on an individual-by-individual basis. Assume, for this embodiment, that a population of millions of individuals each have a genomics account 118 storing their genomic data, and that each of these individuals also has defined a set of authorization directives 128 that define how and when subsets of his or her genome may be shared with others. Note that it is not necessary for each genomics account 118 to store the same selection of genomic data, so long as each genomics account 118 stores some amount of genomic data for an individual.

Figure 5:
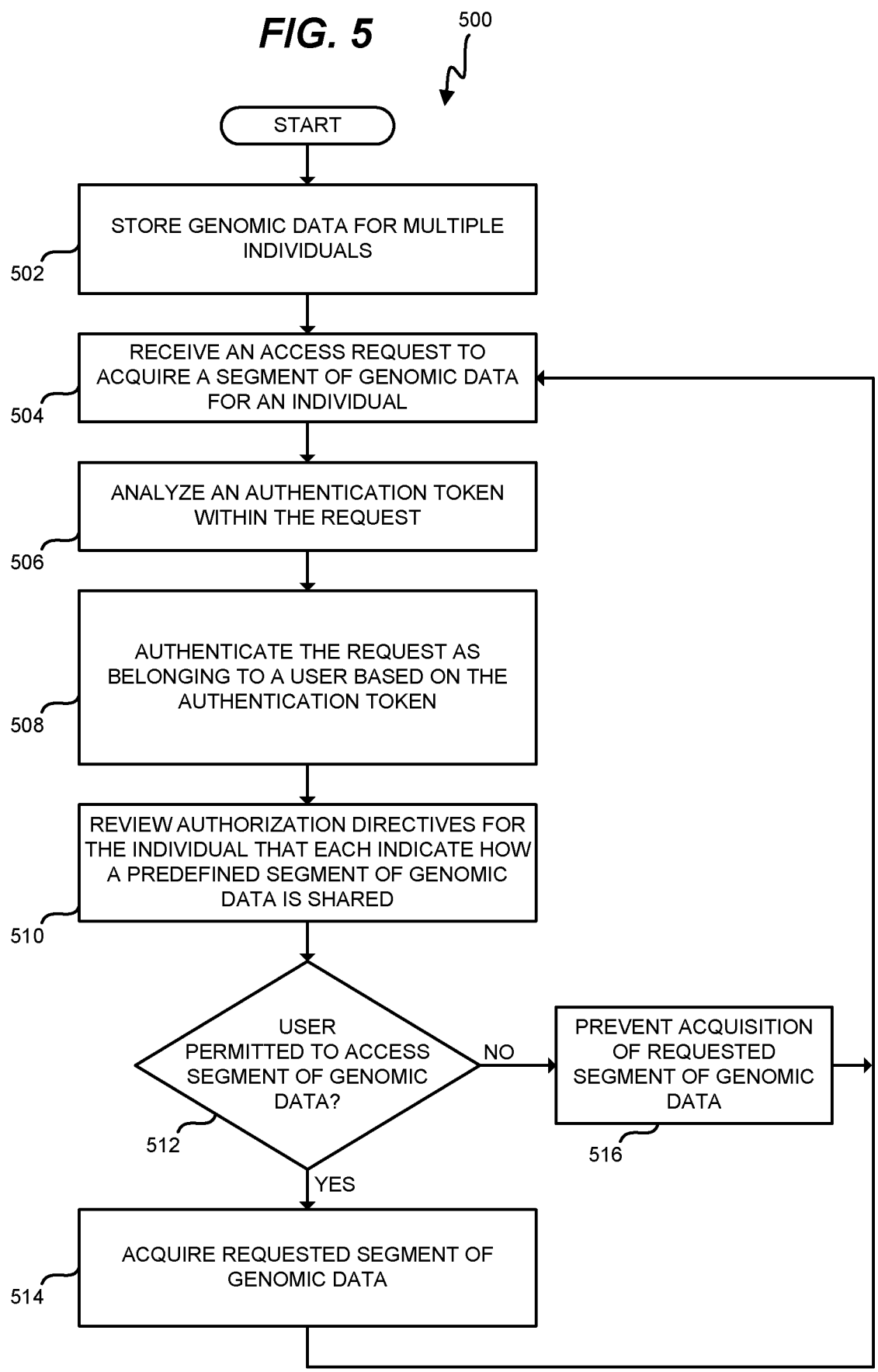
FIG. 5 is a flowchart illustrating a method for operating a genomic sharing system to selectively control sharing of genomic data in an exemplary embodiment.

FIG. 5 is a flowchart illustrating a method 500 for operating genomic sharing system 100 to selectively control sharing of genomic knowledge in an exemplary embodiment. The steps of method 500 are described with reference to genomic sharing system 100 of FIG. 1, but those skilled in the art will appreciate that method 500 may be performed in other systems. The steps of the flowcharts described herein are not all inclusive and may include other steps not shown. The steps described herein may also be performed in an alternative order.

In step 502, controller 114 of genomic data server 110 stores genomic data (e.g., genotypes) for multiple individuals. For example, individuals may register with genomic authorization server 120 to generate accounts for storing genomic data determined via genetic testing. The genomics accounts 118 may then be populated with the genomic data. Each new user may also define a set of authorization directives 128 for their genomics account 118, and may update their authorization directives 128 as desired. For example, a user may update his or her set of authorization directives 128 to enable sharing of genomic data with a potential life partner for a limited period of time, or to enable sharing of genomic data with a specific application.

At some point in time, a user operates device 130 in order to retrieve genomic data. Device 130 generates an access request to acquire one or more segments of genomic data belonging to one or more target individuals. The access request indicates one or more SNPs 224, genes 222, and/or genetic panels 220. The access request may even be directed to an entire genome or exome. The access request may be directed to a specific individual, may be directed to a list of individuals, may be directed to all individuals who have a specific genetic variant (or combination of genetic variants), may be directed to genomics accounts 118 that have specific categorical tags, or may be directed to individuals who have a specific characteristic.

The access request indicates the account that is requesting the genomic data. Furthermore, the access request may be submitted as an encrypted message, and may include an authentication token (e.g., a key of a cryptographic key pair, a password, a biometric parameter, etc.). In one embodiment, the access request includes a keyphrase (e.g., on a Quick Response (QR) code provided by the target individual) that corresponds with an authorization defined by the target individual.

In step 504, controller 124 of genomic authorization server 120 receives the access request at I/F 126 by way of network 150. Controller 124 analyzes an authentication token within the access request in step 506. Furthermore, controller 124 authenticates the access request as belonging to the account based on the authentication token in step 508. In this step, controller 124 identifies the account that is requesting access, and reviews authentication directives 129 to select an authentication key 410 corresponding with the account. Controller 124 may then cryptographically compare the authentication token in the access request.

After the access request has been authenticated as belonging to the account, controller 124 proceeds to determine whether or not the account is authorized to access the requested genomic data for an individual indicated in the request. Thus, controller 124 reviews a set of authorization directives 128 for the individual in step 510. In step 512, controller 124 determines whether the requesting account has permission to access the requested segments of genomic data from genomics account 118. Controller 124 may engage in this process by determining whether criteria listed in an authorization 310 for the segments of genomic data have been met.

If the requesting account is granted access by an authorization 310, then controller 124 proceeds to step 514. In step 514, controller 124 acquires the requested segments of genomic data from genomics account 118. Alternatively, if the requesting account does not have permission to access the requested segments of genomic data, then controller 124 proceeds to step 516, and prevents acquisition of the requested segments of genomic data. In embodiments where each access request pertains to multiple individuals (e.g., by referring to a tag, or a list of individuals), steps 510-516 may be repeated for each individual to determine whether to share genomic data on a person-by-person basis. After genomic data has been acquired (or restricted) for each individual indicated in the access request, controller 124 operates I/F 126 to selectively transmit genomic data to device 130. Specifically, I/F 126 transmits any genomic data that the user is authorized to access.

Method 500 provides a substantial benefit over prior systems and techniques, because it allows for individualized, highly specific, and targeted sharing of genomic data. This ensures that the genetic variants found within an individual are not overshared. Oversharing may be undesirable or even dangerous to the individual.

Figure 6:
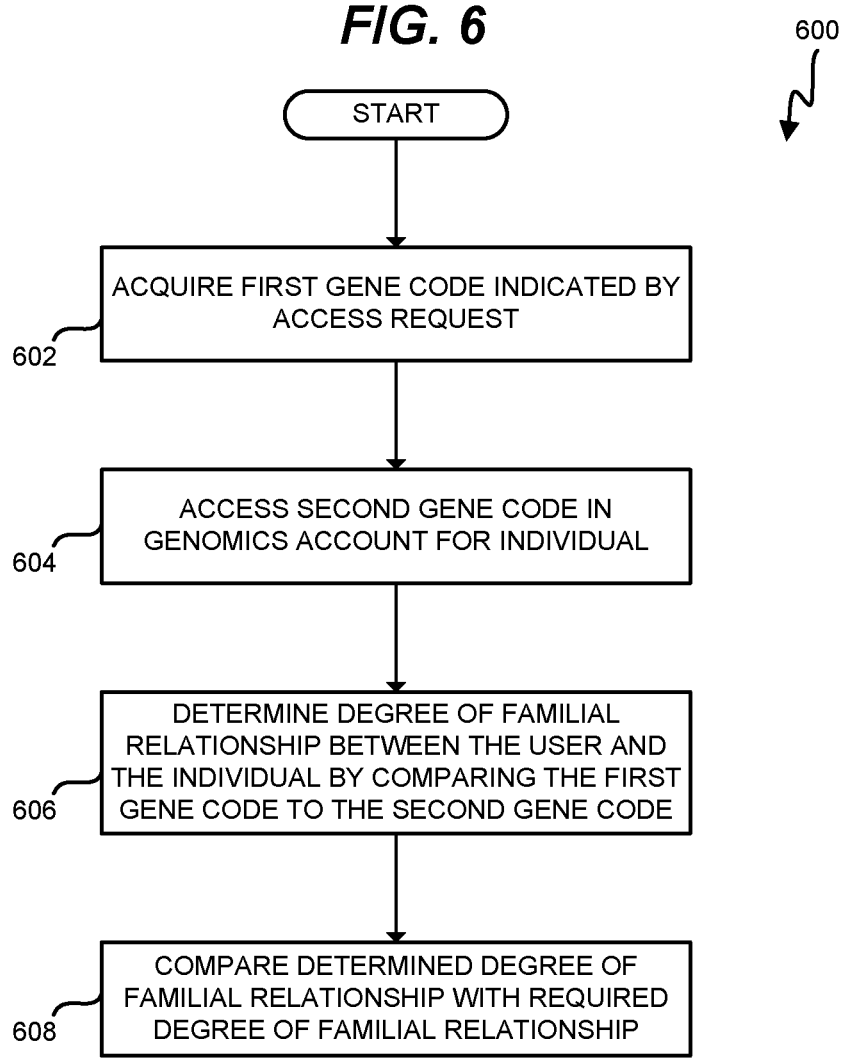
FIG. 6 is a flowchart illustrating a technique for authorizing access to genomic data based on familial relationships determined based upon shared genetic variants in an exemplary embodiment.

FIG. 6 is a flowchart illustrating a technique for authorizing access to genomic data based on familial relationships in an exemplary embodiment. Specifically, method 600 provides details indicating how authorization may be granted by comparing genomic data between the requesting user and a target individual in order to determine whether a familial relationship (e.g., an ancestor/descendent relationship) exists. Method 600 may be performed, for example, during steps 510-512 of method 500 of FIG. 5.

In this embodiment, the access request indicates a first gene code. The access request may indicate the first gene code by including the first gene code, or by pointing to the first gene code as stored at a genomics account 118 for the user. This first gene code lists genetic variants found within the user that originated the access request. The first gene code may recite the contents of an entire exome or genome, or may comprise a predefined selection of genes and/or SNPs associated with one or more haplotypes. Controller 124 accesses the first gene code in step 602.

Controller 124 also accesses a second gene code in the genomics account 118 for the target individual in step 604. Like the first gene code, the second gene code may recite an entire exome or genome, or may comprise a predefined selection of genes and/or SNPs. Each gene code may therefore comprise thousands, or even millions of SNPs. Note that the gene codes do not need to include the same combination of SNPs and/or genes, so long as at least some genomic data exists which may be directly compared between the gene codes.

In step 606, controller 124 proceeds to determine a degree of familial relationship between the user and the target individual, by comparing the first gene code to the second gene code. The specific implementation may vary depending upon whether full genomes and/or exomes are compared, or individual SNPs are compared. In embodiments where full genomes and/or exomes are compared, distributions of shared DNA between different types of relatives may be determined as described in "Variation in actual relationship as a consequence of Mendelian sampling and linkage," by Hill, W G & Weir, Genetics Research, vol. 93, no. 1, pages 47-64 (2011). These distributions are utilized to set thresholds of similarity that determine different levels of familial relationship. These thresholds each indicate a number or percentage of matching alleles (i.e., alleles of the same type) between gene codes.

Familial relationships may be determined based on matching SNPs alone when the entire genome or exome sequence is not available, or when the time/processing load for analyzing the entire genome (or exome) is untenable. In such embodiments, matching SNPs may comprise alleles that have a shared Identity By State (IBS), such as an IBS-2 state. The number (or percentage) of matching SNPs may then be compared with a predefined threshold number (or percentage). For example, one threshold may indicate an immediate family member relationship (e.g., a sibling relationship, parent/child relationship, etc.), while another threshold may indicate an extended familial relationship (e.g., cousin/uncle, grandparent/grandchild, etc.). The threshold needed to ensure a specific level of familial relationship (i.e., degree of relatedness) between the user and the individual may be predefined based on known distributions of DNA within populations.

To further refine the analysis, certain patterns in matching SNPs may indicate a specific degree of relationship. For example, segmental sharing of one allele on all chromosomes may be indicative of a half-sibling or avuncular relationship. A third degree of relationship, such as first cousins, may exist when segmental single allele sharing occurs on half of the chromosomes. In a further embodiment, the existence of genome-wide IBS-0 states indicates no relationship exists. Further analysis techniques may be utilized as described in "Visualization of shared Genomic Regions and Meiotic Recombination in High-Density SNP Data," by Elisha D. O. Roberson and Jonathan Pevsner, PLoS ONE, vol. 4, issue 8, pages 1-13 (August, 2009)

The number of SNPs that are compared may be chosen to ensure a desired degree of prediction accuracy. For example, by increasing the number of compared SNPs, the accuracy of the determined familial relationship will increase. Furthermore, in order to ensure that relationships between persons of different genetically defined sexes may be determined, SNPs in autosomal DNA may be utilized for the analysis process.

Although the analysis in some embodiments is restricted to autosomal DNA, further analysis techniques may consider additional factors for those who have the same genetically defined sex. For example, if the requesting user and the target individual are both male, then genomic data in the Y chromosome may be compared. If the requesting user and the target individual have a potential mother-child relationship, then genomic data in the X chromosome may be compared. In further embodiments, if the user is a potential descendant of a female target individual (or vice versa), mitochondrial DNA (mtDNA) may be utilized for the comparison.

The value of each matching SNP may be weighted. For example, SNPs with low population allele frequencies may be more heavily weighted than other SNPs. A net score across all compared SNPs may then be compared to a threshold score to determine the level of familial relationship.

With the degree of familial relationship determined in step 606, controller 124 compares the determined degree of familial relationship with a required degree of familial relationship indicated in an authorization 310 in step 608. If the determined degree of familial relationship is equal to or closer in relationship than the required degree indicated in the authorization 310, then access may be granted.

Figure 7:
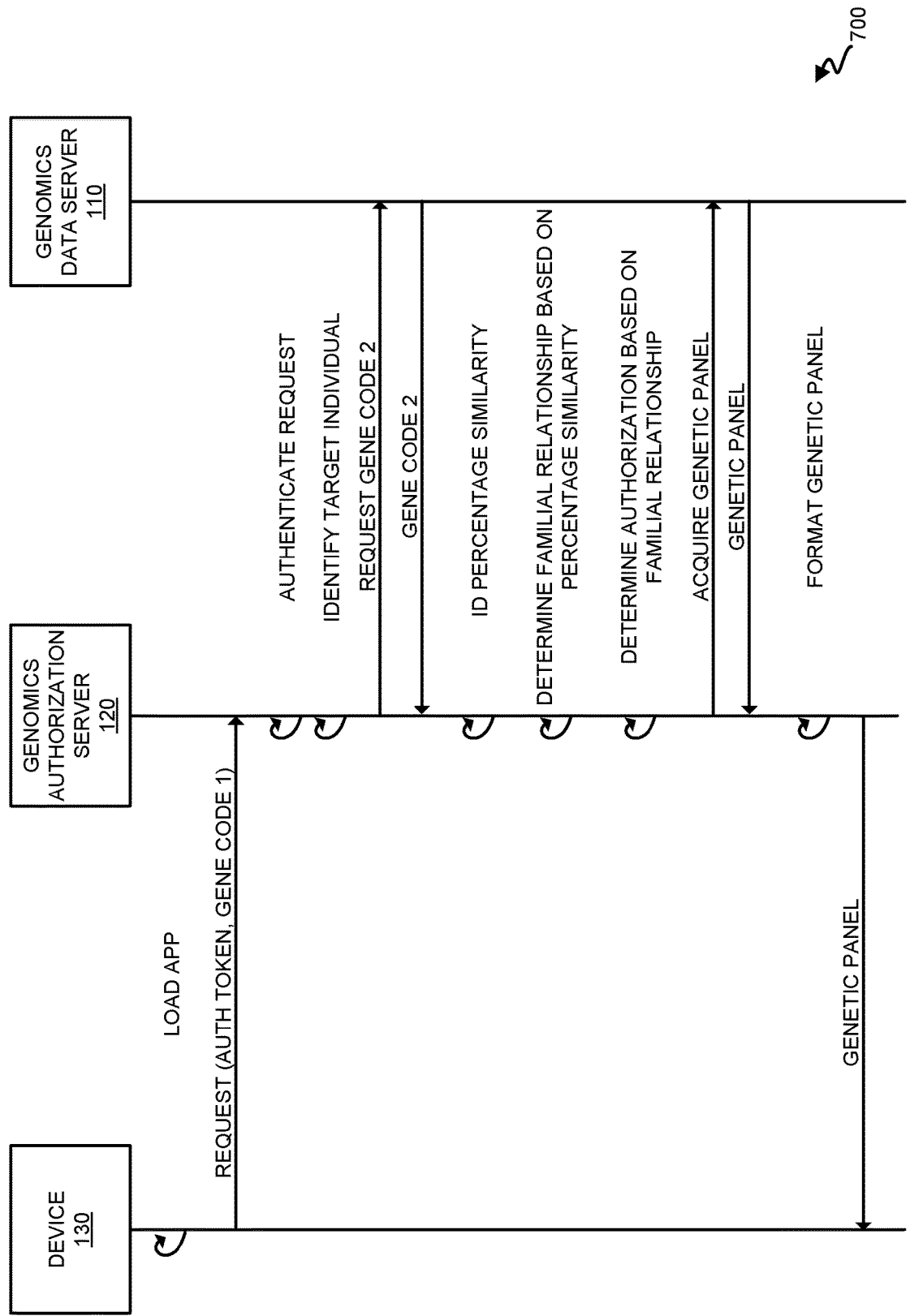
FIG. 7 is a message diagram illustrating communications according to the method of FIG. 6 in an exemplary embodiment.

FIG. 7 is a message diagram illustrating communications according to method 600 of FIG. 6 in an exemplary embodiment. According to FIG. 7, a user of device 130 loads an application at device 130, and the application generates an access request to acquire genomic data for a target individual. The access request is transmitted to genomics authorization server 120, which authenticates the request, identifies the target individual indicated by the request, and requests a second gene code from genomic data server 110 that pertains to the target individual. Upon receiving the second gene code, genomics authorization server 120 identifies SNPs that are described in both the first gene code and the second gene code. Genomics authorization server 120 further proceeds to determine a percentage of identified SNPs that match. Based on the percentage of matching SNPs, a familial relationship is determined, and authorization is granted based on this familial relationship. Upon determining that the user is authorized, genomics authorization server 120 requests a gene panel from genomic data server 110, formats the panel (e.g., by encrypting the panel to ensure that data is not intercepted during transit, and/or to indicate time limits of authorized access for the panel), and transmits the genetic panel to device 130 for use by the application.

Figure 8:
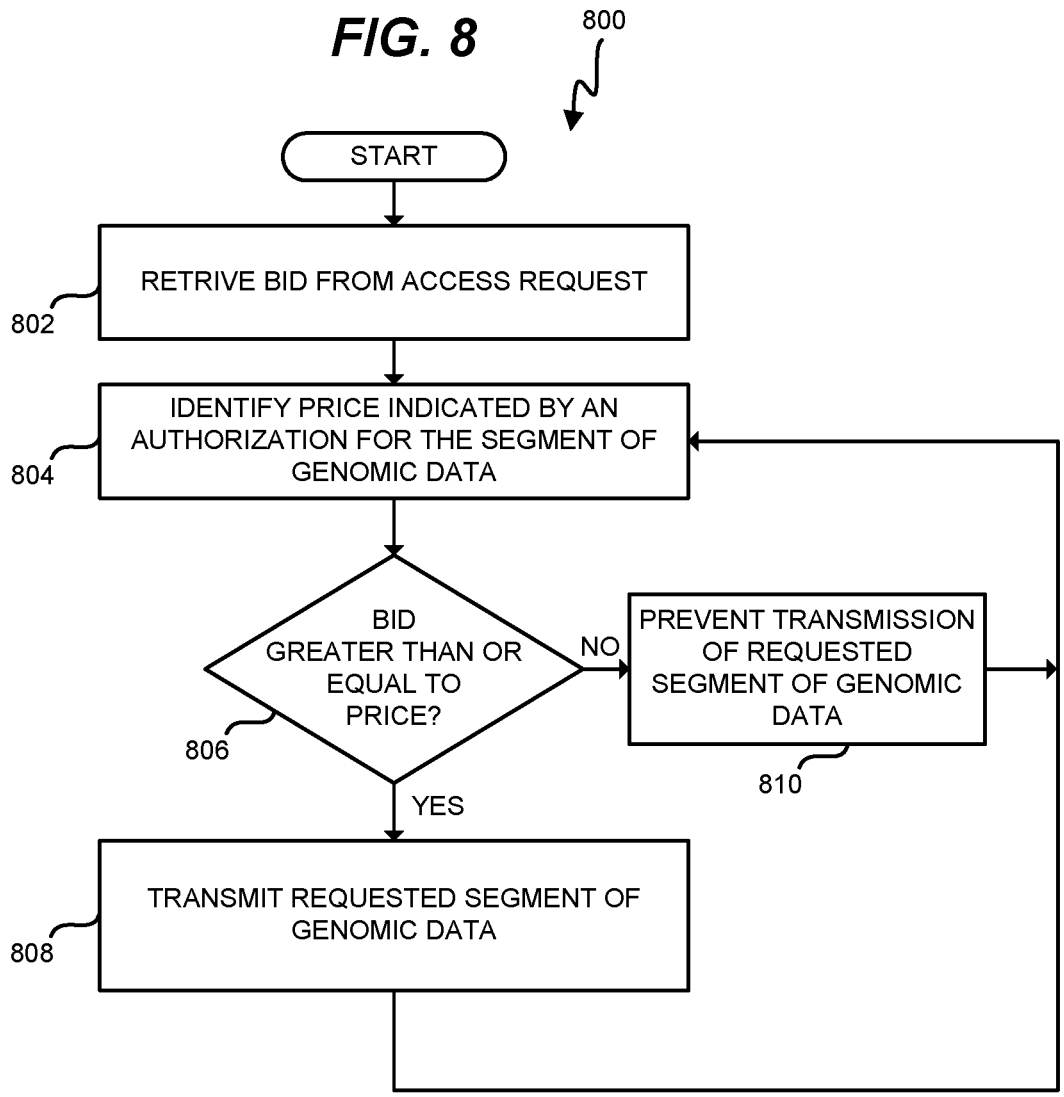
FIG. 8 is a flowchart illustrating an auction-based technique for authorizing sharing of genomic data in an exemplary embodiment.
Figure 9:
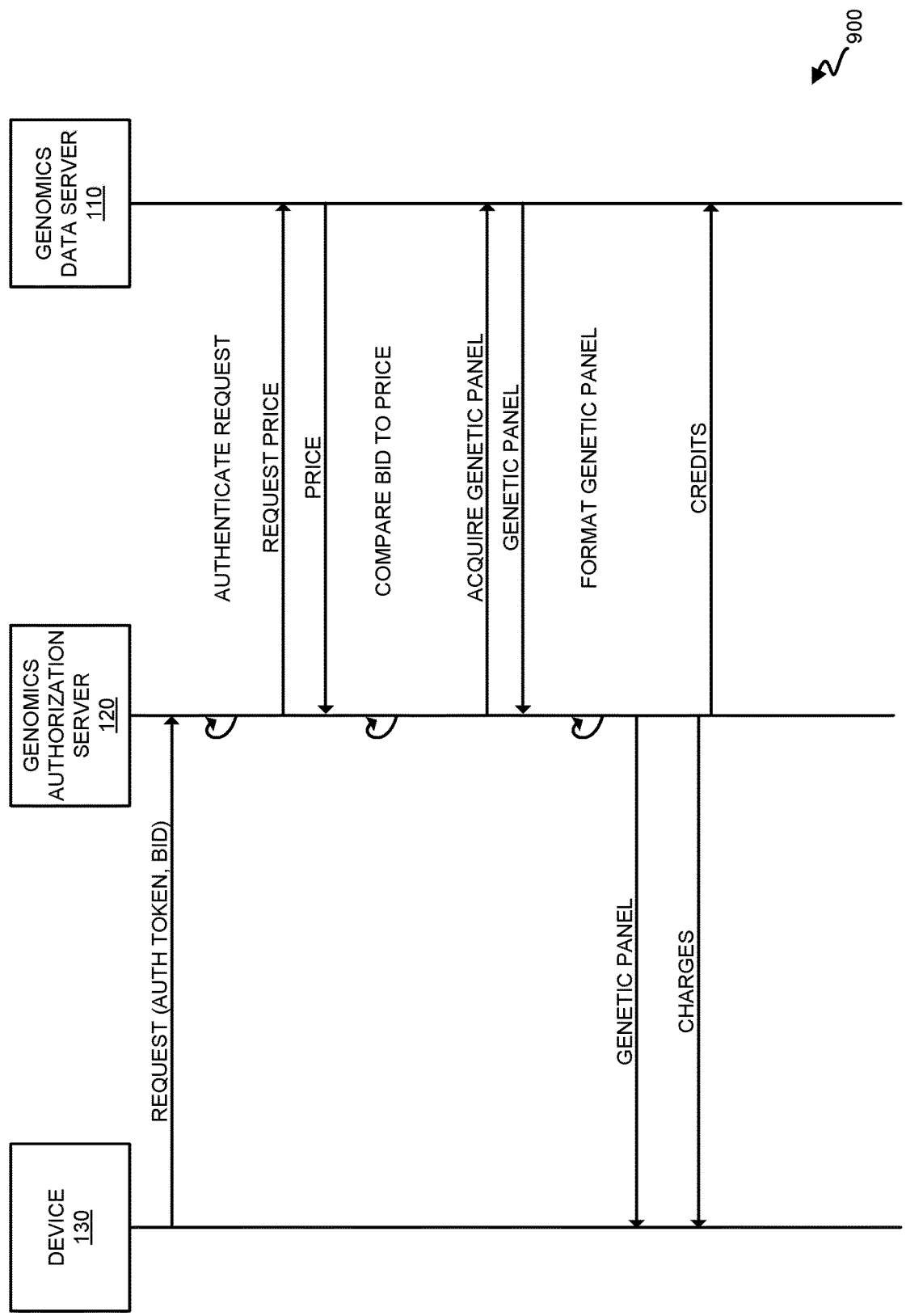
FIG. 9 is a message diagram illustrating communications according to the method of FIG. 8 in an exemplary embodiment.

While FIGS. 6-7 discuss techniques for granting authorization based on familial relationships, FIGS. 8-9 describe auction techniques that enable individuals to selectively share genomic data based on price-related criteria.

FIG. 8 is a flowchart illustrating an auction-based method 800 for authorizing sharing of genomic data in an exemplary embodiment. These techniques may help to facilitate the sharing of genomic data within a marketplace where researchers seek out genomic data for individuals having a known genotype and/or phenotype. In this embodiment, each genomics account 118 includes an authorization 310 with payment criteria 319. Payment criteria 319 defines a price at which specified segments of genome 210 of an individual may be shared. Together, the payment criteria 319 for various individuals forms a marketplace for genomic data pertaining to an entire population of individuals.

Users may provide access requests that indicate desired segments of genomic data (e.g., a combination of genetic panels, genes, and/or SNPs), and/or characteristics (e.g., phenotypes) to retrieve across a population of individuals. The population may be all individuals with genomics accounts 118 on genomic data server 110, or may be individuals within the population who match criteria indicated in the access request, such as individuals that have a desired combination of characteristics (e.g., phenotypes) and genotypes. For example, an access request may be directed to all individuals who have a specific genetic variant of a first gene, and who have a specific phenotype (e.g., brown hair). The access request may then request a segment of genomic data describing a second gene and a third gene within each of those individuals. The access requests also include a bid which the user is willing to pay each individual for access to the requested segment of genomic data.

According to method 800, controller 124 of genomics authorization server 120 retrieves a bid from an access request in step 802. Controller 124 also identifies a price indicated by an authorization 310 for the segment of genomic data for an individual in step 804. In step 806, controller 124 compares the bid to the price. If the bid is equal to or greater than the price, then controller 124 transmits the requested segment of genomic data for the individual to the user that originated the access request in step 808. Alternatively, if the bid is less than the price, controller 124 prevents transmission of the requested segment of genomic data to the user in step 810. Controller 124 may perform steps 804-810 for each of multiple individuals as desired.

In further embodiments, a bid may include a desired sample size (i.e., number of individuals) and a total price (e.g., instead of a per unit price). In such embodiments, controller 124 may selectively acquire segments of genomic data from genomics accounts 118 such that the aggregated cost to the user remains equal to or below the total price. For example, controller 124 may provide segments of genomic data from genomics accounts 118 that have the lowest price for the requested segments (or that are flagged as free), until the sample size is achieved. If the resulting total price exceeds the total price defined by the user, then the access request may be denied in its entirety, and no expenses are generated for the user. This ensures that those requesting genomic data will be able to ensure predictability in cost.

In further embodiments where access requests provide criteria indicating a genotype and/or phenotype from which to acquire genomic data, controller 124 may identify candidates who match the criteria, and may allow the user to independently select candidates from which to acquire genomic data. In such embodiments, each candidate may be accompanied by additional information (e.g., an age, a state/city of residence, or other characteristics) that helps the user to decide whether or not to select the candidate. This may ensure that the user receives genomic data from the proper target individuals, and that recruitment for genetic studies is performed as desired.

FIG. 9 is a message diagram illustrating communications according to method 800 of FIG. 8 in an exemplary embodiment. According to FIG. 9, device 130 prepares and transmits an access request to genomics authorization server 120 that includes a bid. Genomics authorization server 120 authenticates the request, and commands that genomic data server 110 provide pricing information for the requested segment. Genomic data server 110 responds with a message indicating a price associated with the requested segment of genomic data for each individual. Genomics authorization server 120 compares the prices to the bid, and selects a group of individuals having authorizations 310 that permit access to the segment of genomic data at or below the amount of the bid. Genomics authorization server 120 then proceeds to request segments of genomic data (in this case, genetic panels 220) for the group of individuals. Genomics authorization server 120 receives the requested segments of genomic data, formats the segments into a message, and transmits the message to device 130, along with a set of charges to be paid for the provided genomic data. Such charges may include a processing fee. Genomics authorization server 120 also generates a message to genomic data server 110, indicating credits to be provided to users of the genomics accounts 118 from which segments of genomic data were harvested.

FIGS. 5-9 discuss various techniques for operating genomic sharing system 100 of FIG. 1 to ensure that genomic data is shared in granular and carefully tailored manner that ensures privacy. In contrast, FIGS. 10-11 below illustrate message formats via which segments of genomic data may be exchanged.

FIG. 10 is a block diagram illustrating a customized Variant Call Format (VCF) file 1000 that includes sharing parameters in an exemplary embodiment. In this embodiment, genomics authorization server 120 provides segments of genomic data as VCF files. VCF file 1000 includes multiple lines 1050 that follow header line 1040. Each of the multiple lines corresponds with a piece of genomic data for an individual. VCF file 1000 has been modified to include a meta-information line 1010 (included after the characters "##") with a key-value pair that defines a number of days that a recipient of the VCF file is allowed to use information in the VCF file. After the number of days from the file date has expired, a program utilizing the VCF file may delete the VCF file or otherwise prevent access to genomic data stored therein. In further embodiments, line 1010 may indicate a number of times that access is granted, a list of authorized accounts, or other parameters found within the authorizations 310 of FIG. 3. VCF file 1000 also includes a format line 1020 which indicates a genetic panel associated with each piece of genomic data in the VCF file, and a filter line 1030 indicating which pieces of genomic data may be provided via a bidding/auction process. In further embodiments, additional format lines may be utilized to indicate the specific individual that each piece of genomic data describes.

FIG. 11 is a block diagram illustrating a customized Browser Extensible Data (BED) file 1100 that includes sharing parameters in an exemplary embodiment. BED file 1100 describes how genomic data in a binary BED file (not shown) is formatted when it is displayed. Hence, BED file 1100 does not include the genomic data itself, but rather describes how data in an accompanying binary BED file may be shared. BED file 1100, and the accompanying binary BED file, may be transmitted to authorized users via genomics authorization server 120.

As shown in FIG. 11, BED file 1100 includes multiple annotations which are introduced by header lines 1110. Each header line 1110 includes a name and a description. In this case, each header line 1110 indicates a date after which genomic data in a custom track (i.e., genomic data following the header line 1110) becomes restricted and unavailable for use. In further embodiments, header lines 1110 may indicate a number of times that access is granted, a list of authorized accounts, or other parameters found within the authorizations 310 of FIG. 3. The specific segments of genomic data are indicated by lines 1120 following each header line 1110. In this embodiment, a specific date at which authorization is lost for a first track is indicated in one header line 1110.

However, a header line 1110 for a second track indicates that the second track of genomic data may be shared in perpetuity with the user.

EXAMPLES

In the following examples, additional processes, systems, and methods are described in the context of a genomic sharing system 100 that facilitates sharing of genomic data.

In a first example, two persons (Sarah and Thomas) are considering sharing their genomic data with each other in order to allow a baby prediction application to predict possible genetic profiles and associated phenotypes for their future children. These predictive determinations may include, for example, a phenotype of the baby, any potential genetic diseases of the baby, etc. Sarah and Thomas each have a genomics account 118 at genomic data server 110. Sarah elects to share an allergy genetic panel with Thomas, and a phenotype genetic panel with Thomas. Thomas elects to share a fitness genetic panel with Sarah, and an appearance genetic panel with Sarah. Both persons update their authorizations by adding a new authorization 310 permitting access by the other for a limited three month period. When Sarah loads a baby prediction application on a device 130 comprising a laptop, the application contacts genomics authorization server 120 with an access request, which is authenticated by genomics authorization server 120. Genomics authorization server 120 then provides a response that includes genetic panels for appearance and fitness. Upon receiving this information, the application processes the genetic panels, along with segments of Sarah's genome, and makes predictions about the appearance and fitness of a resulting baby between Sarah and Thomas.

In a similar fashion to Sarah, when Thomas loads a baby prediction application on a device 130 comprising a mobile phone, the application contacts genomics authorization server 120 with an access request, which is authenticated by genomics authorization server 120. However, Sarah's authorization includes a device list 316 that prohibits the sharing of genomic data via mobile phones. Hence, Thomas tries again with a device 130 comprising a laptop. Genomics authorizations server 120 then provides a response to Thomas' laptop that includes genetic panels for appearance and allergies. Upon receiving this information, the application processes the genetic panels, along with segments of Thomas' genome, and makes predictions about the appearance and allergy risk (e.g., peanut allergy risk) for the baby based on both Sarah's and Thomas' genetic data.

At the end of the three month period, if Thomas or Sarah attempt to utilize the baby prediction application again, access requests from their devices 130 are authenticated, but not authorized by controller 124 and hence genomic data is no longer shared. Furthermore, on Sarah's device, the application identifies locally stored genomic data for Thomas, and either locks or deletes the genomic data when the authorization period expires. Similarly, on Thomas' devices, the application identifies locally stored genomic data for Sarah, and either locks or deletes the genomic data when the authorization period expires.

In a second example, a researcher wishes to engage in non-profit research to identify whether or not genetic variants of specific genes are correlated with a rare genetic disorder. Thus, the researcher utilizes genomic sharing system 100 in order to acquire genomic data that will be used for the study. First, the researcher opens an application on genomic sharing system 100, and utilizes a Graphical User Interface (GUI) at device 130. Within the GUI, the researcher indicates that the request is for non-profit research. The researcher also indicates that the request is to acquire segments of genomic data only from individuals who have a specific genetic variant at the SNP rs4133274 locus on chromosome 8q24. The researcher, who is based in Colorado, also adds criteria to select only individuals who presently reside in Colorado.

The specific segments of genomic data requested by the researcher correspond with the SNP rs4133275 locus on chromosome 8q24, and the rs3122651 locus on chromosome 4q16. The researcher also requests to be informed of any known allergies for the individuals. The researcher indicates a bid of five hundred dollars per individual, and requests a sample size of fifty. The application at device 130 generates an access request including an authentication token for the researcher, and transmits the access request to genomic authorization server 120 for processing.

Genomic authorization server 120 authenticates the access request. Genomics authorization server 120 also queries genomics data server 119 to determine that one hundred and forty individuals have genomics accounts with the desired segments of genomic data and are located in Colorado. Eighty six of those individuals permit access to the requested segments of genomic data at or below the value of the bid. For example, several of the individuals are willing to provide their genomic data for free when used for non-profit purposes. Genomic authorization server 120 then generates a summary providing anonymized data describing these eighty six individuals, and transmits the summary to device 130.

The researcher at device 130 reviews the summary and selects fifty individuals to utilize for the study, based on the summary. In this example, the summary indicates a city of residence of the individual, a sex of the individual, an age of the individual, and a price of genomic data for the individual. The summary does not include the requested segments of genomic data, nor does it include personally identifiable information for the individuals. That is, the names, mailing addresses, and/or other information identifying the individuals is scrubbed or anonymized. The researcher selects fifty of the individuals via the GUI, and operates device 130 to transmit a selection message to genomics authorization server 120. Genomics authorization server 120 receives the selection message, acquires the requested segments of genomic data from the individuals, and transmits the requested segments of genomic data to the researcher. The requested segments of genomic data are accompanied by information indicating the allergies of the selected individuals.

The researcher reviews a billing message from genomics authorization server 120. The amount to be paid is based on charges from each selected individual, as well as a servicing charge from genomics data server 110. The researcher pays the bill, and the newly received information is unlocked for use at device 130 for research purposes. Upon payment, genomic data server 110 updates genomics accounts for the selected individuals to provide credits to those individuals.

Figure 12:
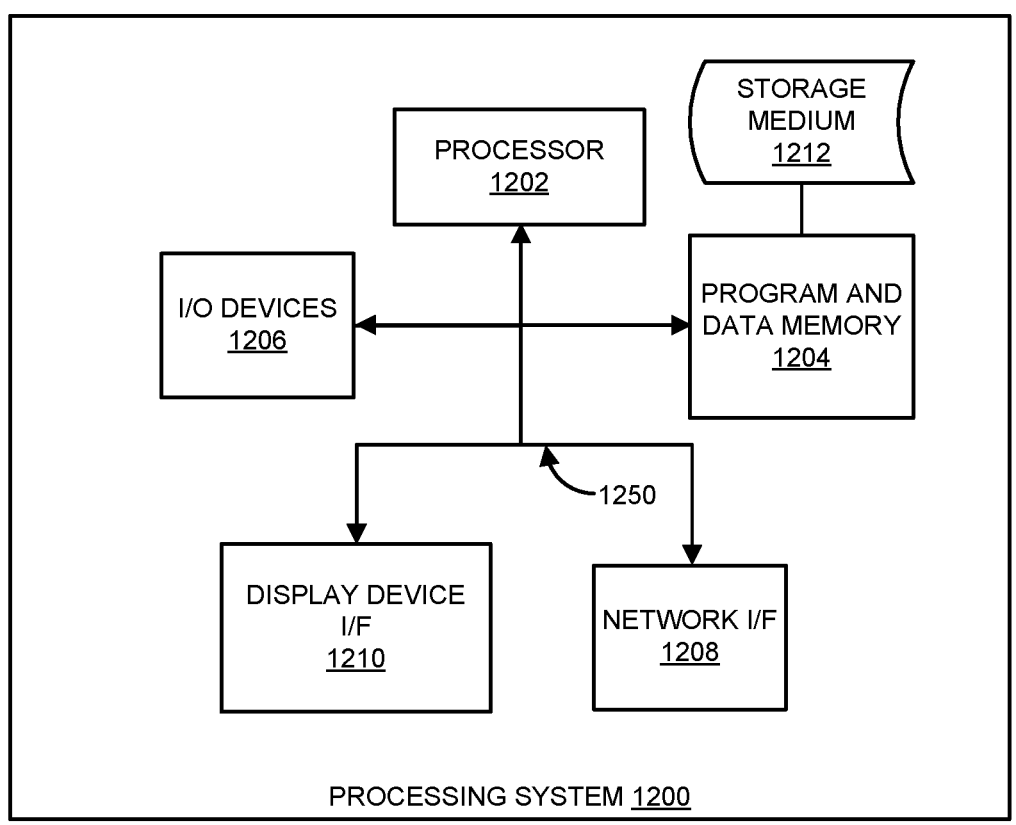
FIG. 12 illustrates an exemplary processing system operable to execute programmed instructions embodied on a computer readable medium.

Embodiments disclosed herein can take the form of a hardware processor implementing programmed instructions, as hardware, as firmware operating on electronic circuitry, or various combinations thereof. In one particular embodiment, software is used to direct a processing system of genomic data server 110, genomics authorization server 120 and/or device 130 to perform the various operations disclosed herein. FIG. 12 illustrates an exemplary processing system 1200 operable to execute a computer readable medium embodying programmed instructions. Processing system 1200 is operable to perform the above operations by executing programmed instructions tangibly embodied on computer readable storage medium 1212. In this regard, embodiments of the invention can take the form of a computer program accessible via computer readable medium 1212 providing program code for use by a computer (e.g., processing system 1200) or any other instruction execution system. For the purposes of this description, computer readable storage medium 1212 can be anything that can contain or store the program for use by the computer (e.g., processing system 1200).

Computer readable storage medium 1212 can be an electronic, magnetic, optical, electromagnetic, infrared, or semiconductor device, or other non-transitory computer readable medium. Examples of computer readable storage medium 1212 include a solid state memory, a magnetic tape, a removable computer diskette, a random access memory (RAM), a read-only memory (ROM), a rigid magnetic disk, and an optical disk. Current examples of optical disks include compact disk-read only memory (CD-ROM), compact disk-read/write (CD-R/W), and DVD.

Processing system 1200, being used for storing and/or executing the program code, includes at least one processor 1202 coupled to program and data memory 1204 through a system bus 1250. Program and data memory 1204 can include local memory employed during actual execution of the program code, bulk storage, and cache memories that provide temporary storage of at least some program code and/or data in order to reduce the number of times the code and/or data are retrieved from bulk storage during execution.

Input/output or I/O devices 1206 (including but not limited to keyboards, displays, pointing devices, etc.) can be coupled either directly or through intervening I/O controllers. Network adapter interfaces 1208 can also be integrated with the system to enable processing system 1200 to become coupled to other data processing systems or storage devices through intervening private or public networks. Modems, cable modems, IBM Channel attachments, SCSI, Fibre Channel, and Ethernet cards are just a few of the currently available types of network or host interface adapters. Display device interface 1210 can be integrated with the system to interface to one or more display devices, such as printing systems and screens for presentation of data generated by processor 1202.

What is claimed is:

1. A system comprising:
a genomic data server that stores genomic data for multiple individuals, the genomic data listing genetic variants determined to exist within the multiple individuals on an individual-by-individual basis; and
a genomic authorization server comprising:
an interface that receives an access request via a computer network for a segment of genomic data for each of multiple individuals, wherein the access request is directed to the segment of genomic data, and the segment of genomic data is selected from the group consisting of: Single Nucleotide Polymorphisms (SNPs), genes, and genetic panels; and
a controller that cryptographically compares an authentication token within the request with an authentication key, the controller determines, based on the comparing, whether the request is authenticated as belonging to an account for a specific user,
if the controller determines that the request is authenticated, the controller determines whether or not the account is authorized to access the segment of genomic data for each individual of the multiple individuals, by:
accessing a first gene code comprising genetic variants determined to exist within the specific user, accessing a second gene code comprising a set of genetic variants determined to exist within an individual of the multiple individuals, determining a degree of familial relationship between the specific user and the individual by comparing the first gene code to the second gene code, and determining whether authorization directives that are particularized for the individual permit the specific user to access the segment of genomic data by comparing the determined degree of familial relationship with a required degree of familial relationship, wherein the authorization directives particularized for the individual indicate the required degree of familial relationship; and
for each individual, the controller transmits the segment of genomic data via the computer network if the authorization directives authorize the account to access the segment of genomic data; and
prevents transmission of the segment of genomic data if the authorization directives do not authorize the account to access the segment of genomic data.

2. The system of claim 1 wherein:
the required degree of familial relationship comprises an avuncular relationship.

3. The system of claim 1 wherein:
the authorization directives indicate time periods during which access to genomic data is permitted.

4. The system of claim 1 wherein:
the controller determines whether the request is authenticated is based on authentication directives that each include an authentication key and account descriptor, and the authentication directives are distinct from the authorization directives.

5. The system of claim 1 wherein:
the genomic data for each individual comprises genes and Single Nucleotide Polymorphisms (SNPs) that are assigned to categorized genetic panels; and
categories for the genetic panels include at least one of fitness, sleep, cancer, maternity, appearance, or ancestry.

6. The system of claim 1 wherein:
the access request includes a bid indicating a price that the user is willing to pay for the segment of genomic data;
at least one of the authorization directives indicates a price for the segment of genomic data; and
the controller determines that the authorization directives permit the user to access the segment of genomic data if the bid meets or exceeds the price.

7. The system of claim 1 wherein:
the controller transmits the segment of genomic data by generating a Variant Call Format (VCF) file, populating the VCF file with the segment of genomic data, modifying the VCF file to include a meta-information line defining a key-value pair indicating a time period during which the segment of genomic data is permitted for use by the user, and directing the interface to transmit the modified VCF file.

8. The system of claim 1 wherein:
the controller transmits the segment of genomic data by generating a Browser Extensible Data (BED) file, populating the BED file with the segment of genomic data, modifying the BED file to include custom track with a header line indicating a time period during which the segment of genomic data is permitted for use by the user, and directing the interface to transmit the modified BED file.

9. A method comprising:
storing genomic data for multiple individuals, the genomic data listing genetic variants determined to exist within the multiple individuals on an individual-by-individual basis;
receiving, via a computer network, an access request for a segment of genomic data for each of multiple individuals, wherein the access request is directed to the segment of genomic data, and the segment of genomic data is selected from the group consisting of: Single Nucleotide Polymorphisms (SNPs), genes, and genetic panels;
cryptographically comparing an authentication token within the request with an authentication key;
determining, based on the comparing, whether the request is authenticated as belonging to an account for a specific user;
if the request is authenticated, determining whether or not the account is authorized to access the segment of genomic data for each individual of the multiple individuals, by:
accessing a first gene code comprising genetic variants determined to exist within the specific user, accessing a second gene code comprising a set of genetic variants determined to exist within an individual of the multiple individuals, determining a degree of familial relationship between the specific user and the individual by comparing the first gene code to the second gene code, and determining whether authorization directives that are particularized for the individual permit the specific user to access the segment of genomic data by comparing the determined degree of familial relationship with a required degree of familial relationship, wherein the authorization directives particularized for the individual indicate the required degree of familial relationship; and
for each individual:
transmitting the segment of genomic data via the computer network if the authorization directives authorize the account to access the segment of genomic data; and
preventing transmission of the segment of genomic data if the authorization directives do not authorize the account to access the segment of genomic data.

10. The method of claim 9 wherein:
the required degree of familial relationship comprises an avuncular relationship.

11. The method of claim 9 wherein:
the authorization directives indicate time periods during which access to genomic data is permitted.

12. The method of claim 9 wherein:
determining whether the request is authenticated is based on authentication directives that each include an authentication key and account descriptor, and the authentication directives are distinct from the authorization directives.

13. The method of claim 9 wherein:
the genomic data for each individual comprises genes and Single Nucleotide Polymorphisms (SNPs) that are assigned to categorized genetic panels; and
categories for the genetic panels include at least one of fitness, sleep, cancer, maternity, phenotype, or ancestry.

14. The method of claim 9 wherein:
the access request includes a bid indicating a price that the user is willing to pay for the segment of genomic data;
at least one of the authorization directives indicates a price for the segment of genomic data; and
the method further comprises determining that the authorization directives permit the user to access the segment of genomic data if the bid meets or exceeds the price.

15. The method of claim 9 further comprising:
generating a Variant Call Format (VCF) file;
populating the VCF file with the segment of genomic data;
modifying the VCF file to include a meta-information line defining a key-value pair indicating a time period during which the segment of genomic data is permitted for use by the user; and
transmitting the modified VCF file.

16. The method of claim 9 further comprising:
generating a Browser Extensible Data (BED) file;
populating the BED file with the segment of genomic data;
modifying the BED file to include custom track with a header line indicating a time period during which the segment of genomic data is permitted for use by the user; and
transmitting the modified BED file.

17. A non-transitory computer readable medium embodying programmed instructions which, when executed by a processor, are operable for performing a method comprising:
storing genomic data for multiple individuals, the genomic data listing genetic variants determined to exist within the multiple individuals on an individual-by-individual basis;
receiving, via a computer network, an access request for a segment of genomic data for each of multiple individuals, wherein the access request is directed to the segment of genomic data, and the segment of genomic data is selected from the group consisting of: Single Nucleotide Polymorphisms (SNPs), genes, and genetic panels;
cryptographically comparing an authentication token within the request with an authentication key;
determining, based on the comparing, whether the request is authenticated as belonging to an account for a specific user;
if the request is authenticated, determining whether or not the account is authorized to access the segment of genomic data for each individual of the multiple individuals, by:
accessing a first gene code comprising genetic variants determined to exist within the specific user, accessing a second gene code comprising a set of genetic variants determined to exist within an individual of the multiple individuals, determining a degree of familial relationship between the specific user and the individual by comparing the first gene code to the second gene code, and determining whether authorization directives that are particularized for the individual permit the specific user to access the segment of genomic data by comparing the determined degree of familial relationship with a required degree of familial relationship, wherein the authorization directives particularized for the individual indicate the required degree of familial relationship; and
for each individual:

transmitting the segment of genomic data via the computer network if the authorization directives authorize the account to access the segment of genomic data; and preventing transmission of the segment of genomic data if the authorization directives do not authorize the account to access the segment of genomic data.

18. The medium of claim 17 wherein:

the required degree of familial relationship comprises an avuncular relationship.

19. The medium of claim 17 wherein:

the authorization directives indicate time periods during which access to genomic data is permitted.

20. The medium of claim 17 wherein:

determining whether the request is authenticated is based on authentication directives that each include an authentication key and account descriptor, and the authentication directives are distinct from the authorization directives.

* * * * *